(12) United States Patent
Wang et al.

(10) Patent No.: US 10,485,736 B2
(45) Date of Patent: Nov. 26, 2019

(54) MULTILAYER-COLOR COMPOSITE MATERIAL FOR USE IN DENTAL DEPARTMENT, AND PREPARATION METHOD THEREFOR

(71) Applicant: Shenzhen Upcera Dental Technology Co., Ltd, Shenzhen (CN)

(72) Inventors: Hongjuan Wang, Shenzhen (CN); Yuexiu Qiu, Benxi (CN); Lianjun Sheng, Shenzhen (CN); Feng Shi, Shenzhen (CN)

(73) Assignee: Shenzhen Upcera Dental Technology Co., Ltd, Shenzhen (CN)

( * ) Notice: Subject to any disclaimer, the term of this patent is extended or adjusted under 35 U.S.C. 154(b) by 86 days.

(21) Appl. No.: 15/576,615

(22) PCT Filed: Dec. 31, 2015

(86) PCT No.: PCT/CN2015/100274
§ 371 (c)(1),
(2) Date: Nov. 22, 2017

(87) PCT Pub. No.: WO2017/080092
PCT Pub. Date: May 18, 2017

(65) Prior Publication Data
US 2018/0161251 A1 Jun. 14, 2018

(30) Foreign Application Priority Data

Nov. 12, 2015 (CN) .......................... 2015 1 0772785

(51) Int. Cl.
| | |
|---|---|
| *A61K 6/083* | (2006.01) |
| *C08K 3/36* | (2006.01) |
| *C08K 3/40* | (2006.01) |
| *B32B 5/00* | (2006.01) |
| *C08F 220/18* | (2006.01) |
| *A61K 6/02* | (2006.01) |
| *A61C 13/00* | (2006.01) |

(52) U.S. Cl.
CPC ............ *A61K 6/083* (2013.01); *A61K 6/0265* (2013.01); *C08F 220/18* (2013.01); *C08K 3/36* (2013.01); *C08K 3/40* (2013.01); *A61C 13/0022* (2013.01)

(58) Field of Classification Search
CPC ................................................. A61K 6/0265
See application file for complete search history.

(56) References Cited

U.S. PATENT DOCUMENTS

| 6,660,194 B1* | 12/2003 | Arita ...................... A61C 13/20 |
| | | 264/16 |
| 8,962,709 B2* | 2/2015 | Bowman .................. A61K 6/00 |
| | | 522/118 |
| 9,687,325 B2* | 6/2017 | Park .................... A61C 13/0022 |
| 9,687,421 B2* | 6/2017 | Toriyabe ................ A61K 6/083 |
| 2005/0154081 A1* | 7/2005 | Yin ......................... A61K 6/083 |
| | | 523/115 |
| 2009/0148813 A1* | 6/2009 | Sun ..................... A61C 13/0001 |
| | | 433/201.1 |
| 2010/0311858 A1* | 12/2010 | Holmes ................. A61K 6/0017 |
| | | 522/47 |
| 2014/0363777 A1* | 12/2014 | Kalgutkar ............ A61K 6/0008 |
| | | 433/2 |

FOREIGN PATENT DOCUMENTS

| CN | 1593371 | 3/2005 |
| CN | 101244013 | 8/2008 |
| CN | 102285795 | 12/2011 |
| CN | 103356391 | 10/2013 |
| CN | 104844200 | 8/2015 |
| JP | 2001-137263 | 5/2001 |
| JP | 2002-128622 | 5/2002 |
| JP | 2004-035332 | 2/2004 |
| JP | 2007-314539 | 12/2007 |
| JP | 2015-531646 | 11/2015 |

OTHER PUBLICATIONS

Office Action issued in Japanese Patent Application No. 2018-524514, dated Oct. 12, 2018 (Machine Translation).
International Search Report issued in PCT Application No. PCT/CN2015/100274, dated Aug. 18, 2016.
Office Action issued in Chinese Application No. 201510772785.9, dated Sep. 6, 2017.

* cited by examiner

*Primary Examiner* — Tae H Yoon
(74) *Attorney, Agent, or Firm* — Norton Rose Fulbright US LLP

(57) ABSTRACT

A method for preparing a multilayer-color composite material for use in dental department comprises: preparing multiple types of monochromatic composite material precursor powder different in color, carrying out dry-pressing and preforming on the precursor powder, so as to obtain a preformed green body; and then carrying out pressurization and heating processing on the preformed green body, so as to obtain a multilayer-color composite material that gradually changes in color from neck portions to incisal ends of teeth, so that the multilayer-color composite material has a higher similarity to the material of natural teeth.

17 Claims, No Drawings

MULTILAYER-COLOR COMPOSITE MATERIAL FOR USE IN DENTAL DEPARTMENT, AND PREPARATION METHOD THEREFOR

This application is a national phase under 35 U.S.C. § 371 of International Application No. PCT/CN2015/100274, filed Dec. 31, 2015, which claims the benefit of priority of Chinese Patent Application No. 201510772785.9 ("Multilayer-color composite material for use in dental department, and preparation method therefor") filed on Nov. 12, 2015. The entire contents of each of the above-referenced applications are incorporated into the present application by reference.

TECHNICAL FIELD

The present invention relates to the field of dental restoration, in particular to a multilayer-colored dental composite material and preparation method therefor.

BACKGROUND ART

Computer Aided Design/Computer Aided Manufacture (CAD/CAM) technology was firstly introduced to the design and manufacture of fixed dental restoration by French professor Francois Duret in the early 70s of 20th century, and it triggered a significant technical revolution in dental restoration field. Whereby, CAD refers to the product design process in which computer is utilized to generate or handle various digital and graphical information; CAM refers to the product manufacturing process performed by CNC (Computer Numerical Control) machining equipment, such as automatic processing and shaping CNC milling machine. Currently, CAD/CAM can be utilized to fabricate various fixed dental restorations, such as inlay, veneer, bridge, and fixed bridge. Nevertheless, patients usually need to pay 2-3 visits to hospital for accomplishing the whole session; such frequent and complex revisit brings tremendous inconvenience for patient. With the development of computer technology, Chair-Side Dental CAD/CAM is now available for rapid treatment.

In Chair-side Dental CAD/CAM system, the CAD/CAM equipment is placed next to dental chair. After tooth preparation by dentist, the tooth model of patient is achieved through digital technology. Through computer, the data can be analyzed, and the denture (restoration) is designed. Finally, the restoration can be automatically fabricated through milling machine. It will only take about 30 minutes for a patient to accomplish the whole treatment course, and complex further consultation can be avoided. In Chair-side Dental CAD/CAM system, the temporary restoration is no longer necessary, and the dental restoration can be prepared directly. Therefore, the demand for clinic visit is reduced, and the quality of dental restoration is obviously improved. By means of model scanning, both design and manufacture of restoration can be performed and accomplished via digital technology, thus, the restoration can be achieved more precisely and accurately, and the success rate of restoration treatment is enhanced. Problems caused by PFM (Porcelain Fused to Metal) denture and removable denture, such as gingival discoloration and marginal unfitness, are largely reduced, and the patient satisfaction for treatment effect is remarkably improved.

The development of Chair-side Dental CAD/CAM technology brings higher requirements for related dental materials. Not only should the material have favorable machinability, thus, the milling time for materials can be shut down to 20 minutes, but also, the time for after-milling process should be very short, thus, the whole restoration treatment can be finished in one doctor appointment. Although traditional zirconia all-ceramic restoration material is also machinable for CAD/CAM system (Non-Chair-side ones), but it is impossible to accomplish the seat of dental restoration in a single doctor visit time due to 6-8 hours sintering time after milling. Presently, dental material used for Chair-side Dental CAD/CAM, developed or being developed, includes glass ceramic (feldspar, leucite, and lithium silicate glass ceramic) and composite material. The composite material is composed of polymer and filler, and it is a relatively ideal dental restoration material due to its favorable toughness, machinability, wear resistance, and X-ray resistance. However, composite materials in prior art are monochromatic. As for nature tooth, color gradually changes from cervical portion to incisal portion. Compared with nature tooth, dental restoration fabricated from monochrome composite cannot repeat the gradient color of nature tooth and thus is short of aesthetic effect.

SUMMARY

The similarity of color between dental restoration produced by monochrome composite material and natural tooth is low. In order to overcome this problem, the present invention discloses a multilayer-colored dental composite material and preparation method therefor. The technical solution is as follows:

Firstly, the present invention provides a preparation method of multilayer-colored dental composite material, which comprises:

a) preparing N monochrome composite precursor powders with different colors, N≥3; wherein, the preparation process for each of monochrome composite precursor powders comprise:

mixing polymer monomer matrix, inorganic filler, initiator, coloring agent, and grinding additive and milling for 0.5-2 h, then drying to obtain monochrome composite precursor powder; wherein, the weight ratio of the polymer monomer matrix to the inorganic filler is 10:90-90:10, preferably 15:85-30:70, the initiator is 0.1%-1%, preferably 0.2%-0.5% by weight of the polymer monomer matrix, and the coloring agent is 0.01%-0.2%, preferably 0.03%-0.1% by weight, based on the total weight of the polymer monomer matrix and the inorganic filler;

b) adding one monochrome composite precursor powder into a dry-pressing mould, and then adding another monochrome composite precursor powder into the dry-pressing mould successively after planishing the previously added powder, until N monochrome composite precursor powders with different colors are all added into the dry-pressing mould; pre-moulding by dry-pressing at a pressure of 3-20 MPa to obtain a pre-moulding green body of multilayer-color composite material;

or b') performing a first pre-mouldings by dry-pressing at a pressure of 3-20 MPa on N monochrome composite material precursor powders respectively, to obtain N monochrome pre-moulding green bodies; then adding all the N monochrome pre-moulding green bodies into the mould successively, and performing a second pre-moulding by dry-pressing at a pressure of 3-20 MPa to obtain a pre-moulding green body of multilayer-colored composite material;

c) pressurizing and heating the pre-moulding green body of multilayer-colored composite material prepared in step b) or b') to obtain multilayer-colored dental composite material, wherein, the pressurizing and heating is performed at a temperature of 100-200° C., preferably 120-180° C., more preferably 130-150° C. for 0.5-3 h, preferably 1-1.5 h.

In one embodiment of the present invention, the pressurizing and heating in step c) is performed at a pressure of 10-200 MPa, preferably 10-20 MPa or 100-200 MPa, more preferably 130-180 MPa, most preferably 150-170 MPa.

In one embodiment of the present invention, the polymer monomer matrix comprises at least two selected from bisphenol A glycidyl dimethacrylate (BIS-GMA), bisphenol A ethyoxylglycidyl methacrylate (BIS-EMA), urethane dimethylacrylate (UDMA), and triethylene glycol dimethacrylate (TEGDMA).

Preferably, the polymer monomer matrix comprises bisphenol A glycidyl dimethacrylate (BIS-GMA), urethane dimethylacrylate (UDMA), and triethylene glycol dimethacrylate (TEGDMA). Based on the total weight of the polymer monomer matrixs, bisphenol A glycidyl dimethacrylate (BIS-GMA) is 0-70%, preferably 0-30% by weight; urethane dimethylacrylate (UDMA) is 0-80%, preferably 40%-70% by weight; and triethylene glycol dimethacrylate (TEGDMA) is 0-60%, preferably 20%-40% by weight.

In one embodiment of the present invention, the inorganic filler comprises at least one selected from glass powder and silica; the glass powder comprises at least one selected from barium glass powder and lanthanum glass powder; silica comprises at least one selected from fumed-silica and nano-silica. The glass powder has a particle size of 0.01-10 μm, preferably 0.1-3 μm; silica has a particle size of 0.01-1 μm, preferably 0.03-0.5 μm; and the glass powder has a refractive index of 1.48-1.60, preferably 1.50-1.58.

Preferably, the inorganic filler comprises glass powder and silica. Based on the total weight of inorganic filler, the glass powder is 70%-95% by weight, and silica is 5%-30% by weight.

In one embodiment of the present invention, the initiator comprises at least two selected from benzoyl peroxide, 2, 6-ditertbutyl-4-methylphenol and N,N-dihydroxyethyl-4-methylaniline.

In one embodiment of the present invention, the coloring agent comprises at least one selected from iron oxide red, iron oxide yellow, bismuth yellow, vanadium zirconium yellow, and cerium praseodymium yellow.

In one embodiment of the present invention, pre-moulding by dry-pressing in step b) or b') is performed at a pressure of 4-10 MPa.

In the present invention, the present invention also provides a multilayer-colored dental composite prepared by the above-mentioned method.

The multilayer-colored dental composite material, which is prepared by the method according to the present invention, possesses gradient multilayer-color system. Dental restoration produced from the composite material according to the present invention has better aesthetic effect, and it is able to simulate the gradient color characteristic of natural tooth from cervical portion to incisal portion. Hence, dental restoration with higher similarity to natural tooth can be obtained from the composite material provided by the present invention.

Moreover, the method according to the present invention adopts solidification technology via pressurizing and heating to cure the composite material. The problems caused by residual monomer in composite material are reduced, and the biocompatibility and safety of the composite material are improved effectively.

DETAILED DESCRIPTION

The present invention provides a preparation method of multilayer-colored dental composite material, which comprises the following steps:

a) preparing N monochrome composite precursor powders with different colors, N≥3; wherein, the preparation process for each of monochrome composite precursor powder comprises:

Mixing polymer monomer matrix, inorganic filler, initiator, coloring agent, and grinding additive, and milling for 0.5-2 h, then drying to obtain the monochrome composite precursor powder; wherein, the weight ratio of the polymer monomer matrix to the inorganic filler is 10:90-90:10, preferably 15:85-30:70, the initiator is 0.1%-1%, preferably 0.2%-0.5% by weight of the polymer monomer matrix, the coloring agent is 0.01%-0.2%, preferably 0.03%-0.1% by weight, based on the total weight of the polymer monomer matrix and the inorganic filler.

In one embodiment of the present invention, the polymer monomer matrix comprises at least two selected from bisphenol A glycidyl dimethacrylate (BIS-GMA), bisphenol A ethyoxylglycidyl methacrylate (BIS-EMA), urethane dimethylacrylate (UDMA), and triethylene glycol dimethacrylate (TEGDMA). In one preferably embodiment of the present invention, the polymer monomer matrix comprises bisphenol A glycidyl dimethacrylate (BIS-GMA), urethane dimethylacrylate (UDMA), and triethylene glycol dimethacrylate (TEGDMA); based on the total weight of the polymer monomer matrix, BIS-GMA is 0-70%, preferably 0-30% by weight; UDMA is 0-80%, preferably 40%-70% by weight; TEGDMA is 0-60%, preferably 20%-40% by weight.

In one embodiment of the present invention, the inorganic filler comprises at least one selected from glass powder and silica, wherein, the glass powder comprises at least one selected from barium glass powder and lanthanum glass powder; silica comprises at least one selected from fumed-silica and nano-silica; the glass powder has a particle size of 0.01-10 μm, preferably 0.1-3 μm; silica has a particle size of 0.01-1 μm, preferably 0.03-0.5 μm; and the glass powder has a refractive index of 1.48-1.60, preferably 1.50-1.58. In one preferably embodiment of the present invention, the inorganic filler comprises glass powder and silica; based on the total weight of inorganic filler, the glass powder is 70%-95% by weight, and silica is 5%-30% by weight.

In one embodiment of the present invention, the initiator can comprises at least two selected from benzoyl peroxide, 2, 6-ditertbutyl-4-methylphenol and N,N-dihydroxyethyl-4-methylaniline. In one embodiment of the present invention, when at least any two of them are used in combination as initiators, benzoyl peroxide can be 0.1%-0.3% by weight, 2, 6-ditertbutyl-4-methylphenol can be 0.2%-0.4% by weight, and N, N-dihydroxyethyl-4-methylaniline can be 0.1%-0.3% by weight, based on the polymer monomer matrix.

In one embodiment of the present invention, the coloring agent comprises, but not limits to: at least one selected from iron oxide red, iron oxide yellow, bismuth yellow, vanadium zirconium yellow, and cerium praseodymium yellow.

It can be understood that, for a multilayer-colored composite material, with a higher value of N, the more obvious color gradient and the higher similarity to natural tooth could be achieved, while the corresponding cost is increased; however, with a over low N, for example less than or equal to 2, the material may be unable to present color gradient. In one embodiment of the present invention, N can be decided by a person skilled in the art. In addition, the material chromatic features in the present invention, including color and transparency parameters, can be adjusted by the addition of coloring agent.

In one embodiment of the present invention, the milling additive can be selected from volatile organic solvents, such as methanol, ethanol, acetone, and etc. Milling medium is required during the milling process, and it can be selected from agate and zirconia. During the milling process, the ratio of the total weight of the polymer monomer matrix, inorganic filler, initiator and coloring agent, the total weight of the milling additives, and the total weight of milling mediums can be 1:1:1-3:6:2, preferably 2:4:1. Within the above-mentioned range, the polymer monomer matrix, inorganic filler, initiator, and coloring agent can be uniformly milled and mixed, meanwhile the overmuch addition of the milling additive is avoided, and thus facilitating a subsequent drying treatment. The milling can be performed for 0.5-2 h, preferably 0.5-1 h. In one embodiment of the present invention, the milling can be conducted by ball milling machine, which is commonly used in the art.

After the milling, a drying treatment is conducted to remove the volatile milling additive. In the present invention, the inventors unexpectedly found that, by performing rotary evaporation pre-drying before the drying treatment, not only the evaporation of solvent is accelerated, but also the solid phase layer separation is reduced during statically drying. Therefore, the uniformity of the mixed materials is improved. In one embodiment of the present invention, the pre-drying is performed at a temperature of 20-100° C., preferably 30-80° C., more preferably 40-50° C. for 1-5 h, preferably 2-3 h. The drying treatment is performed at a temperature of 20-100° C., preferably 30-80° C., more preferably 40-60° C., preferably for 2-4 h.

N monochrome composite precursor powders with different colors are prepared by the above-mentioned steps. Pre-moulding by dry-pressing and pressurizing and heating are performed successively in the present invention to obtain multilayer-colored composite material from N monochrome composite precursor powders with different colors. At least two technical solutions for the pre-moulding by dry-pressing are provided as follows:

b) adding one monochrome composite precursor powder into a dry-pressing mould, and then adding another monochrome composite precursor powder into the dry-pressing mould successively after planishing the previously added powder, until N monochrome composite material precursor powders with different colors are all added into the dry-pressing mould; pre-moulding by dry-pressing at a pressure of 3-20 MPa to obtain a pre-moulding green body of multilayer-colored composite material;

b') performing a first pre-moulding by dry-pressing at a pressure of 3-20 MPa on N monochrome composite precursor powders, respectively, to obtain N monochrome pre-moulding green bodies; then adding all the N monochrome pre-moulding green bodies into the mould successively, and performing a second pre-moulding by dry-pressing at a pressure of 3-20 MPa to obtain a pre-moulding green body of multilayer-colored composite material.

The above-mentioned pre-moulding by dry-pressing is preferably performed at a pressure of 4-10 MPa. It should be noted that, the dry-pressing machine used for pre-moulding is commonly used in the art. Suitable equipment can be chosen based on the purpose of present invention, and these equipments will not described in detail in this invention.

c) pressurizing and heating the pre-moulding green body of multilayer-colored composite material prepared in step b) or b') to solidify the polymer monomer matrix, so as to obtain multilayer-colored dental composite material, wherein, the pressurizing and heating is performed at a temperature of 100-200° C., preferably 120-180° C., more preferably 130-150° C., and at a pressure of 10-200 MPa, preferably 10-20 MPa or 100-200 MPa, more preferably 130-180 MPa, most preferably 150-170 MPa for 0.5-3 h, preferably 1-1.5 h.

By means of the above-mentioned pressurizing and heating, the contact area between the polymer monomer matrix and the initiator is increased at a certain pressure. Therefore, the efficient of solidification reaction is enhanced, the residual of monomer is reduced, and the biocompatibility and strength of the composite material are improved effectively.

It should be noted that, the equipment for pressurizing and heating adopted in the present invention is commonly used in the art. Suitable equipments, such as the YJH30-25 equipment from Nantong jianhua company, can be chosen as long as the purpose of present invention can be achieved, and these equipments will not described in detail in the present invention.

The technical solution in the present invention will now be described with reference to the following examples, and the described examples are only a part of examples of the invention, not all of them. Based on the examples of the present invention, all the other examples obtained by one skilled in the art without inventive effort are within the protection scope of the invention.

Example 1

According to the formulas and related process parameters in Table 1 with regard to powders 1-3, all the materials were mixed and ball-milled uniformly, then 3 monochrome composite material precursor powders (i.e., powders 1-3) with different colors were prepared. After that, powder 1 was firstly added to a dry-pressing mould and planished to 4 mm thick, then powder 2 was added successively and planished to 6 mm thick, successively powder 3 was added and planished to 4 mm thick. Then, pre-moulding by dry-pressing was performed via dry-pressing machine at a pressure of 5 MPa to obtain a pre-moulding green body of multilayer-colored composite material. After that, pressurizing and heating the pre-moulding green body of multilayer-colored composite material, wherein the pressurizing and heating were performed at a temperature of 140° C., and a pressure of 150 MPa for 1 h; obtaining multilayer-colored composite material with 3 color gradient layers.

Example 2

According to the formulas and related process parameters in Table 1 with regard to powders 1-3, 3 monochrome composite material precursor powders (i.e., powders 1-3) with different colors were prepared. After that, powders 1-3 were used as raw materials, wherein, powder 1 of 3 mm thick was added to a dry-pressing mould, and pre-moulding by dry-pressing was performed at a pressure of 7 MPa; then powder 2 of 7 mm thick and powder 3 of 4 mm thick were pre-moulded by dry-pressing respectively using the same method; then, all of 3 monochrome pre-moulding green bodies were put into the mould, and the pre-moulding by dry-pressing was performed again at a pressure of 10 MPa to obtain a pre-moulding green body of multilayer-colored composite material.

After that, pressurizing and heating the pre-moulding green body of multilayer-colored composite material was performed at a temperature of 130° C. and a pressure of 170 MPa for 1.5 h, obtaining the multilayer-colored composite material with 3 color gradient layers.

TABLE 1

Formulas and process parameters of 5 monochrome composite material precursor powders with different colors

| | Raw materials and processes | Powder 1 | Powder 2 | Powder 3 | Powder 4 | Powder 5 |
|---|---|---|---|---|---|---|
| Monomer matrix | BIS-GMA | 5 | 4 | — | 2 | 9 |
| | UDMA | 9 | 11 | 20 | 13 | 12 |
| | TEGDMA | 5 | 5 | 5 | 2 | 9 |
| Inorganic filler | Barium glass powder | 75 | — | 75 | 15 | 15 |
| | Lanthanum glass powder | — | 75 | — | 20 | 41 |
| | Fumed-silica | 6 | — | — | — | 14 |
| | Nano-silica | — | 5 | — | 48 | — |
| Initiator | Benzoyl peroxide | 0.019 | 0.05 | 0.05 | 0.02 | 0.1 |
| | 2,6-ditertbutyl-4-methylphenol | — | 0.05 | 0.06 | — | 0.1 |
| | N,N-dihydroxyethyl-4-methylaniline | — | — | 0.065 | 0.14 | 0.1 |
| Coloring agent | Iron oxide red | 0.007 | 0.021 | 0.042 | 0.040 | 0.045 |
| | Iron oxide yellow | 0.003 | — | — | 0.010 | — |
| | Bismuth yellow | — | 0.009 | — | 0.020 | 0.036 |
| | Cerium praseodymium yellow | — | — | 0.018 | — | 0.018 |
| | Weight ratio of polymer monomer matrix to inorganic filler | 19/81 | 20/80 | 25/75 | 17/83 | 30/70 |
| Material mixing | Weight ratio of raw material/grinding ball/ball-milling additive | 2/4/1 | 3/5/1 | 1/1/1 | 2/4/1 | 2/4/1 |
| | Time (h) | 0.5 | 1 | 1.5 | 2 | 1 |
| Pre-drying | Temperature (° C.) | 50 | 50 | 40 | 30 | 40 |
| | Time (h) | 2 | 2.5 | 3 | 3 | 2.5 |
| Drying | Temperature (° C.) | 50 | 50 | 40 | 70 | 60 |
| | Time (h) | 4 | 2.5 | 3.5 | 2 | 4 |

Note:
part by weight was used as the unit for numerical values of monomer matrix, inorganic filler, initiator, and coloring agent, for example, each part by weight can be set as 10 g.

Example 3

According to the formulas and related process parameters in Table 1 with regard to powders 1-5, 5 monochrome composite material precursor powders (i.e., powders 1-5) with different colors were prepared. After that, powders 1-5 were used as raw materials, wherein, powder 1 was firstly added to a dry-pressing mould and planished, and powder 2 was added successively and planished, then powder 3 was added. Do this successively until all the powders 1-5 were added to the dry-pressing mould and planished to 4 mm, 6 mm, 4 mm, 4 mm, and 7 mm thick, respectively. Then, pre-moulding by dry-pressing was performed via dry-pressing machine at a pressure of 10 MPa to obtain a pre-moulding green body of multilayer-colored composite material. After that, pressurizing and heating the pre-moulding green body of multilayer-colored composite material was performed at a temperature of 150° C., and a pressure of 130 MPa for 1.5 h, obtaining the multilayer-colored composite material with 5 color gradient layers.

Example 4

Example 4 differs from Example 1 only in that, pre-moulding by dry-pressing in Example 4 was performed at a pressure of 7 MPa, and pressurizing and heating in Example 4 was performed at a temperature of 140° C., and a pressure of 130 MPa for 1 h.

Example 5

Powders 1-3 were used as raw materials, wherein, powder 1, 2, and 3 were 4 mm, 7 mm, and 3 mm thick, respectively, and all the other process parameters were identical to Example 2.

Example 6

Example 6 differs from Example 2 only in that, pressurizing and heating in Example 6 was performed at a temperature of 180° C., and a pressure of 180 MPa for 0.5 h.

Example 7

Example 7 differs from Example 2 only in that, pressurizing and heating in Example 7 was performed at a temperature of 120° C., and a pressure of 180 MPa for 0.5 h.

Example 8

Example 8 differs from Example 2 only in that, pressurizing and heating in Example 8 was performed at a temperature of 200° C., and a pressure of 100 MPa for 3 h.

Example 9

Example 9 differs from Example 2 only in that, pressurizing and heating in Example 9 was performed at a temperature of 100° C., and a pressure of 200 MPa for 2 h.

Performance Test

Flexural strength, compression strength, and fracture toughness of multilayer-colored composite material prepared in Examples 1-5 were measured respectively, and the results are shown in Table 2.

In the present invention, the measurement of flexural strength was performed according to YY/T 0710-2009/ISO 10477-2004 "Dentistry-Polymer-Based Crown and Bridge Materials"; the measurement of compression strength was performed according to ISO 9917-1-2007; and the measurement of fracture toughness was performed according to ISO 6872-2008.

As shown in Table 2, the composite material prepared in the examples of the present invention holds excellent mechanical properties. During the application of in dental restoration, whether in machining process or in wearing and using process, this composite material can retain excellent morphology due to high strength and toughness, while phenomenon such as chipping or cracking can be avoided. Hence, this material can be widely used in dental restoration field, so as to satisfy the corresponding market requirement.

TABLE 2

Performance of multilayer-colored composite material prepared in Example 1-5

| Example | Flexural strength/MPa | Compression strength/MPa | Fracture toughness/MPa · m$^{1/2}$ |
|---|---|---|---|
| Example 1 | 212.02 ± 2.43 | 550.30 ± 35.69 | 1.58 ± 0.06 |
| Example 2 | 203.58 ± 1.25 | 543.04 ± 29.99 | 1.60 ± 0.24 |
| Example 3 | 200.69 ± 3.64 | 520.65 ± 25.57 | 1.55 ± 0.45 |
| Example 4 | 223.49 ± 3.21 | 566.45 ± 32.86 | 1.54 ± 0.14 |
| Example 5 | 194.87 ± 5.89 | 536.28 ± 19.85 | 1.59 ± 0.36 |

The water absorption, solubility, and chemical solubility of the multilayer-colored composite material prepared in Example 1 and 3M Lava Ultimate CAD/CAM Restorative were measured respectively, and the results are shown in Table 3.

TABLE 3

Performance comparison of product prepared in Example 1 and 3M Lava Ultimate CAD/CAM Restorative (LT)

| Item | Example 1 | 3M |
|---|---|---|
| Water absorption/μg · mm$^{-3}$ | 22.73 | 37.45 |
| Solubility/μg · mm$^{-3}$ | 0.00 | 2.98 |
| Chemical solubility/μg · cm$^{-2}$ | 8.71 | 155.58 |

As shown in Table 3, compared to the product of 3M Lava Ultimate CAD/CAM Restorative, the multilayer-colored composite material prepared in Example 1 possesses remarkably lower water absorption, solubility, and chemical solubility. The above results indicate that the solubility of composite material is reduced, and the biocompatibility and safety of the multilayer-colored composite material can be improved according to the preparation method provided by the present invention.

The multilayer-colored dental composite material and the preparation method therefor provided by the present invention are described in detail as stated above. The principles and embodiments of the present invention are described by adopting individual examples and the illustration of above examples are only used for understanding the method and substantial concept of the present invention. It should be noted that, it is possible for a person skilled in the art to perform several improvements and modifications without departing from the principles of the present invention, these improvements and modifications also fall within the protection scope of the invention as claimed.

The invention claimed is:

1. A method for preparing a multilayer-colored dental composite material, comprising:
a) preparing N monochrome composite precursor powders with different colors, N≥3; wherein, the preparation process for each of the monochrome composite precursor powders comprises:

mixing a polymer monomer matrix, an inorganic filler, an initiator, a coloring agent, and a milling additive, and milling for 0.5-2 h, then drying to obtain a monochrome composite precursor powder; wherein, the weight ratio of the polymer monomer matrix to the inorganic filler is 10:90-90:10, the initiator is 0.1%-1% by weight of the polymer monomer matrix, and the coloring agent is 0.01%-0.2% by weight, based on the total weight of the polymer monomer matrix and the inorganic filler;
b) adding one monochrome composite precursor powder into a dry-pressing mould, and then adding another monochrome composite precursor powder into the dry-pressing mould successively after planishing the previously added powder, until the N monochrome composite precursor powders with different colors are all added into the dry-pressing mould; then pre-moulding by dry-pressing at a pressure of 3-20 MPa to obtain a pre-moulding green body of multilayer-colored composite material; or
b') performing a first pre-moulding by dry-pressing at a pressure of 3-20 MPa on the N monochrome composite material precursor powders, respectively, to obtain N monochrome pre-moulding green bodies; then adding all of the N monochrome pre-moulding green bodies into the mould successively, and performing a second pre-moulding by dry-pressing at the pressure of 3-20 MPa to obtain a pre-moulding green body of multilayer-colored composite material;
c) pressurizing and heating the pre-moulding green body of multilayer-colored composite material prepared in step b) or b') to obtain the multilayer-colored dental composite material, wherein, the pressurizing and heating is performed at a temperature of 100-200° C.

2. The method according to claim 1, wherein the pressurizing and heating is performed at a pressure of 10-200 MPa.

3. The method according to claim 1, wherein the polymer monomer matrix comprises at least two selected from the group consisting of bisphenol A glycidyl dimethacrylate (BIS-GMA), bisphenol A ethyoxylglycidyl methacrylate (BIS-EMA), urethane dimethylacrylate (UDMA), and triethylene glycol dimethacrylate (TEGDMA).

4. The method according to claim 3, wherein the polymer monomer matrix comprises at least two selected from the group consisting of bisphenol A glycidyl dimethacrylate (BIS-GMA), urethane dimethylacrylate (UDMA), and triethylene glycol dimethacrylate (TEGDMA); wherein, bisphenol A diglycidyl methacrylate (BIS-GMA) is 0-70% by weight, urethane dimethylacrylate (UDMA) is 0-80% by weight, and triethylene glycol dimethacrylate (TEGDMA) is 0-60% by weight, based on the total weight of the polymer monomer matrix.

5. The method according to claim 1, wherein the inorganic filler comprises at least one selected from the group consisting of a glass powder and silica; wherein, the glass powder comprises at least one selected from the group consisting of a barium glass powder and a lanthanum glass powder; silica comprises at least one selected from the group consisting of a fumed-silica and a nano-silica; the glass powder has a particle size of 0.01-10 μm; silica has a particle size of 0.01-1 μm; and the glass powder has a refractive index of 1.48-1.60.

6. The method according to claim 5, wherein the inorganic filler comprises the glass powder and silica, wherein the glass powder is 70%-95% by weight, and silica is 5%-30% by weight, based on the total weight of the inorganic filler.

7. The method according to claim 1, wherein the initiator comprises benzoyl peroxide, and N,N-dihydroxyethyl-4-methylaniline.

8. The method according to claim 1, wherein the coloring agent comprises at least one selected from the group consisting of iron oxide red, iron oxide yellow, bismuth yellow, vanadium zirconium yellow, and cerium praseodymium yellow.

9. The method according to claim 1, wherein the pre-moulding by dry-pressing in step b) or b') is performed at a pressure of 4-10 MPa.

10. The method according to claim 1, wherein the weight ratio of the polymer monomer matrix to the inorganic filler is 15:85-30:70, the initiator is 0.2%-0.5% by weight of the polymer monomer matrix, and the coloring agent is 0.03%-0.1% by weight, based on the total weight of the polymer monomer matrix and the inorganic filler.

11. The method according to claim 1, wherein the pressurizing and heating is performed at a temperature of 120-180° C. for 1-1.5 h.

12. The method according to claim 1, wherein the pressurizing and heating is performed at a temperature of 130-150° C. for 1-1.5 h.

13. The method according to claim 1, wherein the pressurizing and heating is performed at a pressure of 10-20 MPa or 100-200 MPa.

14. The method according to claim 1, wherein the pressurizing and heating is performed at a pressure of 130-180 MPa.

15. The method according to claim 1, wherein the pressurizing and heating is performed at a pressure of 150-170 MPa.

16. The method according to claim 4, wherein bisphenol A diglycidyl methacrylate (BIS-GMA) is 0-30% by weight, urethane dimethylacrylate (UDMA) is 40%-70% by weight, and triethylene glycol dimethacrylate (TEGDMA) is 20%-40% by weight, based on the total weight of the polymer monomer matrix.

17. The method according to claim 5, wherein the glass powder has a particle size of 0.1-3 µm; silica has a particle size of 0.03-0.5 µm; and the glass powder has a refractive index of 1.50-1.58.

* * * * *